United States Patent [19]
Tribble et al.

[11] 4,123,519
[45] Oct. 31, 1978

[54] INJECTABLE CONTRACEPTIVE VACCINE AND METHOD

[75] Inventors: Ronald L. Tribble, Savannah; Charles M. Stagg, St. Joseph, both of Mo.

[73] Assignee: Philips Roxane, Inc., St. Joseph, Mo.

[21] Appl. No.: 880,506

[22] Filed: Feb. 23, 1978

Related U.S. Application Data

[63] Continuation of Ser. No. 715,163, Aug. 17, 1976, abandoned.

[51] Int. Cl.² .............................................. A61K 39/00
[52] U.S. Cl. ........................................ 424/88; 424/85; 424/100; 424/105; 424/177; 424/238; 424/243
[58] Field of Search .................... 424/85, 88, 100, 105, 424/177, 238, 243

[56] References Cited
PUBLICATIONS

CA.84 No. 159864r, No. 159865s (1976).
CA.83 No. 191210q, No. 188650c, No. 129524s (1975.
CA.80 No. 23006x, No. 106544x (1974).
CA.79 No. 64420a (1973).
CA.77 No. 56941q (1972).
CA.84 No. 40423f, No. 40425h (1976).
CA.82 No. 122178c, No. 122179d, No. 151517t, No. 151518u, No. 15159v (1975).
CA.81 No. 48386e (1974).
CA.79 No. 51604p, No. 64068s, No. 16679v, No. 112892e (1973).
CA.77 No. 101991u, No. 31179j, No. 147777g, No. 147778h (1972).
CA.76 No. 97742y, No. 138870j (1972).

*Primary Examiner*—Shep K. Rose

[57] ABSTRACT

An injectable contraceptive vaccine, a method of preparing said vaccine and the method of preventing conception in mammals by use of said vaccine, is disclosed. A vaccine which stimulates the production of antibodies directed against a hormone essential to the reproductive cycle of a mammal is prepared by coupling such a hormone to a carrier to form a hormone-carrier conjugate. Conception in mammals is prevented by injection of such vaccine during the proper period of the reproductive cycle of said mammal.

Specifically described is the vaccine prepared by coupling a hormone, such as estradiol-17 beta, with a protein and its use to sterilize a female of the canine species.

4 Claims, No Drawings

INJECTABLE CONTRACEPTIVE VACCINE AND METHOD

This is a continuation of application Ser. No. 715,163 filed Aug. 17, 1976 now abandoned.

SUMMARY OF INVENTION

This invention relates to a contraceptive vaccine, to a method of its preparation and to a process for the prevention of conception in female mammals by the use of such vaccine.

Particularly, the invention relates to a contraceptive vaccine which stimulates the production of antibodies to an estrogen, which estrogen is essential to the reproductive cycle of a female mammal, and which antibodies have been produced by the immunological system of the female mammal.

Still more particularly, the invention comprises a contraceptive vaccine which stimulates the production of antibodies against the estrogen, estradiol-17 beta ($E_2$), when injected into a female mammal such that an antibody level of at least 70 PEA units per ml blood serum exist in such female at the time of expected estrus.

GENERAL DESCRIPTION OF INVENTION

There exists today a considerable interest on the part of those concerned with animal husbandry, and others, in the prevention of conception, at least for some period of time, in most mammals, whether they be primate, canine, feline, bovine, ovine porcine, equine, and the like. Consequently, there have been many methods derived to accomplish this end, all of which are undesirable in one respect or another. For example, clinical surgery (castration, ovari-hysterectomy) has its obvious faults. Mechanical contraception is likewise undesirable for various reasons and chemotherapeutic agents are not only unreliable, but also many times induce undesirable side effects in many mammals.

It has long been known that female mammals produce estrogen which is necessary for the manifestation of estrus, ovulation and implantation. If the mammalian body were to produce its own antibodies against such a requisite estrogen, fertility would not exist.

The natural occurring estrogen molecule in the mammalian body is nonantigenic and therefore will not stimulate the production of antibodies of said estrogen in the body of said mammals.

The present invention involves producing a vaccine which, when injected into a mammal, will stimulate the production of antibodies against a requisite estrogen. This is accomplished by first making an antigen by coupling an essential estrogen to a carrier and injecting such antigen into the mammal to cause sterilization of, or prevent conception in, said mammal.

Of particular interest, and contemplated in one preferred embodiment of this invention, is a contraceptive vaccine which stimulates the production of antibodies against the estrogen, estradiol-17 beta ($E_2$), which vaccine has been found useful to control canine reproduction.

It has been found that if the contraceptive vaccine is given, one can expect a contraceptive effect.

The preparation of the novel contraceptive vaccine of this invention may be generally described as follows.

The vaccine of the present invention comprises a steroid-carrier conjugate which has been found to be effective in producing specific antibodies against the steroid. For example, an estrogen such as estradiol-17 beta($E_2$) is rendered antigenic by covalent attachment to a carrier. The carrier selected for use in the production of the vaccine may be, for example, any protein or polypeptide, which, when combined with the said estrogen molecule, will render the said steroid-carrier conjugate antigenic.

In one specific embodiment of the inventive concept, the conjugation of the estradiol-17 beta ($E_2$) to the amino groups of the carrier used is effected by preparing the hemisuccinate of the estrogen molecule, which hemisuccinate is then coupled to the carrier via the carbodiimide reaction.

As is well known in the art, other estrogens may be rendered antigenic by coupling to other carriers by known chemical reactions. For example, estrogens such as estradiol-17 alpha, estrone, estriol, equilin, equilenin, and the like may be coupled to a carrier which, in itself, may be antigenic, or may be modified to become antigenic. Examples of such carriers are Keyhole Limpet Hemocyanin (KLH), Bovine Serum Albumin (BSA), Human Serum Albumin (HSA), and the like.

A derivative of the desired estrogen is prepared, for example, by esterification of the hydroxyl groups of the estrogen with succinic anhydride, forming the oxime derivatives of the ketone groups of the estrogen using (o-carboxymethyl) hydroxylamine, and the like, and the derivative is then coupled to the carrier by, for example, the Schotten-Baumann method, the mixed anhydride method, the carbodiimide condensation, and the like. These techniques are well known to the art. See for example, Thorneycroft, I. H. (1970). Preparation and Purification of Antibodies to Steroids. Immunologic Methods in Steroid Determination, Appleton-Century-Crofts, 63-86; Lindner, et al. 1972. Specificity of Antibodies to Ovarian Hormones in Relation to the Site of Attachment of the Steroid Hapten to the Peptide Carrier. Steroids 19:357; Mahajan, D. K., et al. 1972. Plasma 11-Deoxycortisol Radioimmunoassay for Metyrapone Tests. Steroids 20:609; Yellin, T. O. 1972. Estradiol-17-Beta-Hemisuccinate: An Improved Procedure. J. Lipid Res. 13:554; Lieberman, et al. 1959. Steroid-Protein Conjuates: Their Chemical, Immunochemical, and Endocrinological Properties. Rec. Prog. Hor. Res. 15:165.

The prior art has also described the use of various estrogen antibodies in the investigation of mechanism of the reproductive cycles of mice, (Ferin, M., et al. 1968. Inactivation of the Biological Effects of Exogenous and Endogenous Estrogens by Antibodies to 17 Beta-Estradiol. Endocrinology 83:565), rats, (Ferin, M. A. et al. 1969. Effect of Antibodies to 17 Beta-Estradiol and Progesterone on the Estrous Cycle of the Rat. Endocrinology 85:1070) and sheep, (Scaramuzzi, R. J. 1975. Inhibition of Oestrous Behaviour in Ewes by Passive Immunization Against Oestradiol-17 Beta. J. Reprod. Fert. 42:145).

The female to be protected is injected with the desired amount of vaccine, parenterally, preferably both intradermally and intramuscularly. After an initial injection, the female may be injected periodically in order to maintain a satisfactory antibody level, and thus maintain sterilization.

PREPARATION OF VACCINE

The vaccine of one preferred embodiment of this invention consists of a steroid-protein conjugate found to be effective in producing specific antibodies against the steroid ($E_2$) residue. Estradiol-17 beta ($E_2$) is rendered antigenic by covalent attachment to the protein Bovine Serum Albumin (BSA). Coupling to epsilon-amino groups of the lysine residues of BSA is affected via the 17-beta hemisuccinate by the use of the carbodiimide reagent. The complete conjugation procedure employed is a modification of procedures employed by previous researchers.

1. Preparation of Estrogen Derivative

Five grams of $E_2$ (Calbiochem, San Diego, Cal.) and 25 microCuries (uCi) of $^3$H-6,7-estradiol-17 beta ($^3$H-$E_2$) (New England Nuclear, Boston, Mass.) are added to a 500 ml round-bottom flask. Next, 250 ml benzene containing 1% pyridine and 15 gm succinic anhydride are added to the same flask and the contents refluxed for 40 hours. The solvent is then evaporated and the remaining residue is dissolved in 625 ml methanol. To the solution is added 100 ml of a 15% solution of sodium bicarbonate and the contents are stirred overnight. The contents are filtered and an equal volume of water is added. The solution is then extracted three times with 200 ml portions of diethyl ether. The remaining aqueous phase is adjusted to pH7 with 6 N HCL and poured into a mixture of 0.2 N HCL and crushed ice (1:1). The precipitate, estradiol-17 beta hemisuccinate ($E_2$-HS), is collected by filtration, washed with water and dried in vacuo at 37° C.

The general chemical scheme leading to the formation of the estradiol-hemisuccinate is as follows:

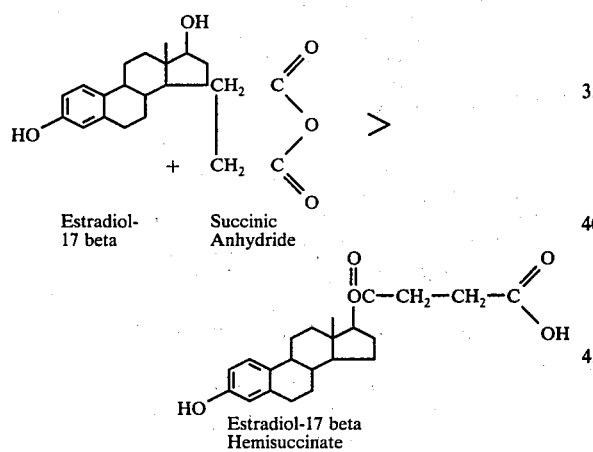

Estradiol-17 beta + Succinic Anhydride

Estradiol-17 beta Hemisuccinate

In order to subsequently determine the number of moles of $E_2$ which are attached to a mole or protein, the disintegrations per minute per mg $E_2$-HS (DPM/mg $E_2$-HS) must be determined. To accomplish this, 45 to 55 mg of accurately weighed $E_2$-HS is placed into a liquid scintillation counting vial. To the vial is also added 0.1 ml water and 1 ml of Soluene-350 (solubilizer, Packard Instrument Co., Downers Grove, Ill.) and the contents are allowed to stand until the residue is completely digested. After this digestion, 10 ml of Dimulume (Scintillation media, Packard Instrument Co.) is added and the contents of the vial are counted for radioactivity. The DPM/mg $E_2$-HS is then determine based upon counts per minute (CPM), scintillation counter efficiency and weight of $E_2$-HS. The DPM/mg $E_2$-HS is calculated in the following manner: Example:

CPM = 90,000
Weight of $E_2$-HS = 50 mg efficiency = 40%

$$DPM = \frac{CPM}{efficiency} = \frac{90,000}{0.4} = 225,000 \text{ DPM/50 mg } E_2\text{-HS}$$

$$DPM/mg\ E_2\text{-HS} = \frac{225,000}{50} = 4500$$

2. Conjugation of Estrogen Derivative to Carrier

Five grams of BSA (Sigma) is dissolved in 250 ml of water the the pH is adjusted to 7.8. With constant stirring, 2.5 gm of water-soluble carbodiimide [1-ethyl-3 (3-di-methyl amino propyl) - carbodiimide] is added while maintaining the above pH dilute HCl. There is added dropwise 50 ml of dimethyl formamide containing 2.5 gm $E_2$-HS with constant stirring while maintaining the pH at 7.8 with 1 N NaOH. The reaction mixture is equilibrated at room temperature for 2 hours, after which an additional 500 mg of the carbodiimide is added. After an additional 20 hour equilibration, the mixture is dialyzed against water for 48 hours. The steroid-protein conjugate is precipitated by the addition of 90 ml acetone for each 10 ml of solution remaining in the dialysis bag. The residue is collected by filtration, washed with acetone and dried in vacuo at 37° C. The general chemical scheme leading to the formation of $E_2$-BSA from $E_2$-HS is as follows:

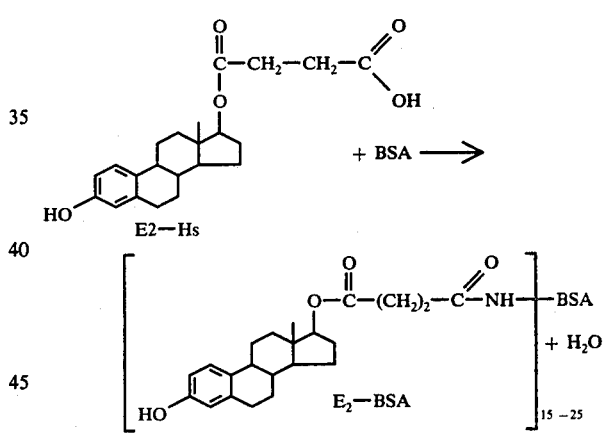

3. Testing of Vaccine

Ten to 15 mg of accurately weighed steroid-protein conjugate ($E_2$-BSA) is placed into a liquid scintillation counting vial. To the vial is added 0.1 ml water and 1 ml of Soluene-350 and the contents are allowed to stand until the residue is completely digested. After this digestion, 10 ml of Dimulume is added and the contents of the vial are counted for radioactivity. The number of moles of $E_2$ which is attached to one mole of BSA is calculated in the following manner:

EXAMPLE:

1. Molecular weight (M.W.) of BSA = $7 \times 10^4$ gm/mole
2. DPM/mg $E_2$-HS as determined under 1. above - 4500 DPM/mg $E_2$-HS
3. M.W. of $E_2$-HS = 372 gm/mole
4. 5300 DPM/10 mg of $E_2$-BSA

Calculations:

$$\frac{5300 \text{ DPM}/10 \text{ mg E}_2\text{-BSA}}{4500 \text{ DPM/mg E}_2\text{-HS}} = 1.18 \text{ mg } (0.00118 \text{ gm}) \text{ E}_2\text{-HS}$$

$$\frac{0.00118 \text{ gm E}_2\text{-HS}}{372 \text{ gm/mole}} = 3.17 \times 10^{-6} \text{ Mole of E}_2\text{-HS}$$

$$\frac{0.010 \text{ gm BSA}}{7 \times 10^4 \text{ gm/Mole}} = 1.43 \times 10^{-7} \text{ Mole of BSA}$$

$$\frac{\text{Moles E}_2\text{-HS}}{\text{Moles BSA}} = \frac{3.17 \times 10^{-6}}{1.43 \times 10^{-7}} = 22$$

It has been found, and forms an important part of the inventive concept, that the $E_2$-BSA antigen is most effective in producing specific antibodies against the steroid moiety when the number of $E_2$-HS molecules incorporated per molecule of BSA is between 15 and 25.

As was stated above, the vaccine of this invention is an $E_2$ protein conjugate, prepared as described above.

Each dog to be protected receives an initial inoculation of 1 mg $E_2$-BSA emulsified in 2 ml of adjuvant with a concentration of 0.5 mg/ml. The adjuvant consists of an emulsion containing by volume:

50% Complete Freund's Adjuvant
50% water

One ml is injected into multi-intradermal sites. The other 1 ml is injected into 2 intramuscular (I.M.) sites.

In order to determine whether the proper antibody levels are maintained, the following assay system has been performed. The serum is titered for antibodies against $E_2$ by the capacity of the serum to bind the radioactive form of $E_2$, $^3$H-6,7-$E_2$ ($^3$H-$E_2$). Serial dilutions of the serum are carried out to obtain and end point binding of approximately 50% of the $^3$H-$E_2$ added. The dilution of serum that gives approximately 50% binding is used to calculate the antibody level. Using the various serum dilutions, a sigmoid curve is obtained and 50% binding fits into the linear most portion of the curve. A charcoal suspension is used to separate antibody-bound $^3$H-$E_2$ from free $^3$H-$E_2$. If one adds 10,000 cpm of $^3$H-$E_2$ and after charcoal separation finds 5000 cpm of $^3$H-$E_2$ bound to the antibody, one therefore achieves a 50% binding at a particular serum dilution.

In order to calculate the amount of $^3$H-$E_2$ found in each tube per dilution, the mass of the original $^3$H-$E_2$ added must be determined as shown in the following calculation.

EXAMPLE:

1. M.W. of $^3$H-$E_2$ = 272.4 gm
2. Specific Activity of $^3$H-$E_2$ = 49.3 Ci/m Mole
3. 2.22 × $10^6$ DPM per uCi
4. CPM $^3$H-$E_2$ added per culture tube = 10,414
5. 1 gm = 1 × $10^{12}$ picograms (pg)
6. Efficiency of counting = 46.6%

Therefore:
1. 49.3 Ci = 49.3 × $10^6$ uCi
2. mMole of $^3$H-$E_2$ = 0.2724 gm (49.3 × $10^6$ uCi) (2.22 × $10^6$ DPM/uCi) = 109.446 × $10^{12}$ DPM/0.2724 gm $$\frac{109.446 \times 10^{12} \text{ DPM}}{0.2724 \text{ gm}} = 401.78 \times 10^{12} \text{ DPM/gm}$$

$$\frac{401.78 \times 10^{12} \text{ DPM/mg}}{1 \times 10^{12 \, pg/gm}} = 401.78 \text{ DPM/pg}$$

$$\text{DPM} = \frac{\text{CPM}}{\text{Efficiency}} = \frac{10,414}{0.446} = 22,348 \text{ DPM}$$

$$\text{Mass (pg) added} = \frac{22,348 \text{ DPM}}{401.78 \text{ DPM/pg}} = 55.6 \text{ pg}$$

Once the mass of the $^3$H-$E_2$ has been determined, the binding capacity of the serum can be calculated as shown in Table I.

TABLE I

| | | Binding Capacity of the Serum | | |
|---|---|---|---|---|
| Serum Dilution (ml) | CPM | % $^3$H-$E_2$ Bound (CPM/10,414) | pg $^3$H-$E_2$ Bound (% bound × 55.6) | Factor | pg $^3$H-$E_2$ Bound per ml serum |

| Serum Dilution (ml) | CPM | % $^3$H-$E_2$ Bound (CPM/10,414) | pg $^3$H-$E_2$ Bound (% bound × 55.6) | Factor | pg $^3$H-$E_2$ Bound per ml serum |
|---|---|---|---|---|---|
| 1/100* | 8346* | 77.9* | 44.2* | × 100 | 4,420* |
| 1/500* | 8147* | 76.0* | 43.2 | × 500 | 21,600* |
| 1/1000 | 7548 | 72.5 | 40.3 | × 1000 | 40,300 |
| 1/2000 | 6182 | 59.4 | 33.0 | × 2000 | 66,000 |
| 1/2500** | 5086** | 48.8** | 27.1** | 2 2500 | 68,000** |
| 1/4000 | 2845 | 27.3 | 15.2 | × 4000 | 60,800 |
| 1/5000 | 2040 | 19.6 | 10.9 | × 5000 | 54,500 |
| 1/10,000 | 797 | 7.7 | 4.3 | × 10,000 | 43,000 |

*Determined from another assay where added CPM = 10,718 and pg = 56.8
**Dilution coming nearest to 50% binding Calculations are based on the reading at the 1/2500 dilution since at this dilution approximately 50% of the $^3$H-$E_2$ is bound. Therefore, 1 ml of the serum has the ability to bind 68,000 pg of $E_2$ or 68,000 pg equivalent antibody (PEA) units.

TREATMENT OF FEMALE MAMMALS

All female dogs to be treated with the vaccine of this invention were selected with known reproductive histories consisting of at least one previously recorded estrus period. The females were injected with either 0.5 or 1.0 mg of the vaccine prepared as described above. Data obtained from 15 treatment cycles representing 9 dogs is set out in Table II below.

TABLE II

Active Immunization with Estradiol-17 Beta-Bovine Serum Albumin ($E_2$-BSA) for Sterilization in the Female Dog

| | Immunization | | A Injection Interval (Mo.)[c] | B Duration of Anti-$E_2$ Levels Above 70 PEA Units (Mo.) | C Theoretical Protection Time (A+B) (Mo.) | D Duration from Pre-Treatment Estrus to Actual Estrus (Mo.) | E Anti-$E_2$ Levels at Actual Estrus (PEA Units) |
|---|---|---|---|---|---|---|---|
| Dog No. | No. of Injections | Amount of $E_2$-$E_{p\,BSA}$ (mg) | | | | | |
| D09 | 1 | 1.0 | 3.25 | 3.00 | 6.25 | 12.25 | <10 |
| D11 | 1 | 0.5 | 3.25 | 3.00 | 6.25 | 8.25 | 40 |
| D11[a] | 1 | 1.0 | 2.25 | 2.00 | 4.25 | 5.75 | <20 |
| D06[b] | 3 | 1.0 | 3.25 | 30.50+ | 33.75+ | 33.75+[e] | — |
| 3370 | 1 | 0.5 | 3.25 | 2.75 | 6.00 | 7.00 | 40 |

TABLE II-continued

Active Immunization with Estradiol-17 Beta-
Bovine Serum Albumin ($E_2$-BSA) for
Sterilization in the Female Dog

| Dog No. | Immunization No. of Injections | Amount of $E_2$-$E_{pBSA}$ (mg) | A Injection Interval (Mo.)[c] | B Duration of Anti-$E_2$ Levels Above 70 PEA Units (Mo.) | C Theoretical Protection Time (A+B) (Mo.) | D Duration from Pre-Treatment Estrus to Actual Estrus (Mo.) | E Anti-$E_2$ Levels at Actual Estrus (PEA Units) |
|---|---|---|---|---|---|---|---|
| 3370[a] | 1 | 1.0 | 3.25 | 3.00 | 6.25 | 6.50 | 60 |
| 4974 | 1 | 1.0 | 3.25 | 1.25 | 4.50 | 7.50 | 40 |
| 5415 | 1 | 1.0 | 3.25 | 3.75 | 7.00 | 7.50 | 45 |
| 5415[a] | 1 | 1.0 | 3.00 | 3.50 | 6.50 | 13.75 | <10 |
| 5458 | 1 | 1.0 | 3.25 | 6.25 | 9.50 | 10.75 | 25 |
| 5458[a] | 1 | 1.0 | 0.25 | 6.75+[d] | 7.00+ | 7.00 | 408 |
| 5795 | 1 | 1.0 | 3.25 | 3.00 | 6.25 | 6.25 | 45 |
| 5795[a] | 1 | 1.0 | 4.25 | 2.00 | 6.25 | 7.50 | 50 |
| 5634 | 1 | 1.0 | 6.00 | 0.50 | 6.50 | 8.75 | <10 |
| 4974[a] | 1 | 1.0 | 3.00 | 0.50 | 3.50 | 7.50 | <10 |

[a]Received $E_2$—BSA following the first post treament estrus
[b]Received a second and third injection of $E_2$—BSA 8½ and 19 months, respectively, following the first injection.
[c]Interval from pre-treatment estrus to injection
[d]Antibody levels were not measured after estrus
[e]This female has not returned to estrus at the time of this writing.

It has been found that the bitch produces at maximum 68.9 ± 11.0 pg of estradiol-17 ($E_2$) per ml serum (Nett et al. 1975. Levels of Luteinizing Hormone, Estradiol and Progesterone in Serum During The Estrous Cycle and Pregnancy in the Beagle Bitch. Proc. Soc. Exp. Biol. Med. 148:134). Therefore, if one administers an estrogen-protein conjugate and stimulates the production of antibodies against $E_2$ (anti-$E_2$) sufficient to bind in excess of 70 pg of $E_2$ per ml serum, one should achieve sterilization of the female dog.

Preliminary studies indeed indicate evidence (Table II) to support the claim that sterilization of the female dog can be brought about by active immunization with administered estrogen-protein conjugate (vaccine).

It can be noted from Table II that with the exception of one treatment cycle (No. 5458, second treatment cycle) at no time did estrus occur when the binding capacity of anti-$E_2$ exceeded approximately 70 pg of $E_2$ per ml of serum. It can be assumed from Table II that if anti-$E_2$ levels were maintained to bind 70 or more pg of $E_2$ per ml of serum, one could obtain a more pronounced contraceptive effect.

If the claim that anti-$E_2$ levels capable of binding 70 or more pg of $E_2$ per ml of serum will elicit a contraceptive response in female dogs is valid, the duration from pre-treatment estrus to actual estrus following treatment (Column D) should exceed the theoretical protection time (Column C). This is indeed the case with the exception of one treatment cycle (No. 5458, second treatment cycle).

The contraceptive effect was noticeably significant in one treatment cycle (No. D06) when anti-$E_2$ levels were maintained for an extended duration by repeated injections of $E_2$-BSA. To further substantiate that the extended duration time of anti-$E_2$ levels capable of binding approximately 70 pg of $E_2$ or more per ml of serum causes an extended contraceptive effect, the following data (Table III) is shown.

TABLE III

Repeated Administration, Every 10 to 14 Days, of Anti-$E_2$ in 12 Female Dogs

| Dog No. | Control (Untreated) Estrous Cycle Lengths Prior to Treatment (Days) | Treatment Cycle Length (Days) | Range of Anti-$E_2$ Titers Throughout the Treatment Period (PEA Units) |
|---|---|---|---|
| 7489 | 226 | 500 | 150–339 |
|  | 238 |  |  |
| 9048 | 252 | 480+ | 103–408 |
| 16825 | — | 457+ | 98–378 |
| 12533 | — | 403 | 66–430 |
| 12889 | — | 600+ | 131–445 |
| 10221 | 234 | 239 | 80–413 |
| 3947 | 256 | 321 | 95–447 |
|  | 162 |  |  |
|  | 222 |  |  |
| 4967 | 311 | 457 | 92–430 |
|  | 255 |  |  |
| 6475 | 199 | 207 | 120–429 |
|  | 189 |  |  |
|  | 176 |  |  |
| 8996 | 159 | 370 | 84–447 |
|  | 193 |  |  |
| 1895 | — | 517+ | 174–469 |
| 12090 | 229 | 306 | 132–453 |
| Avg. | 220 | Avg. 405+ |  |

As shown in Table III, by administering repeated injections of anti-$E_2$ to maintain titers sufficient to bind approximately 70 pg or more of $E_2$ per ml of serum, one can definitely see a contraceptive effect as evidenced by the lengthened treatment cycle (avg. 405+ days) versus the average control cycle length (220 days). Although the anti-$E_2$ was administered passively, the results are still conclusive for the stated claim.

To summarize briefly, this invention is directed to the discovery that a vaccine which stimulates the production of antibodies against an estrogen which is essential to the reproductive cycle of a female mammal can be prepared and used to sterilize the female. This has been graphically illustrated by the use of female dogs as exemplary of the mammals. The concept of the invention may, of course, be applied to other mammalian species such as humans, cows, horses, pigs, and the like, it being necessary only to prepare an antigen which stimulate the production of antibodies against an estrogen which is essential to the reproductive cycle of the species. Although the concept is directed at blocking the reproductive cycle of the female, it is also contemplated that a vaccine which will stimulate the production of antibodies against a necessary hormone to the reproductive process of the male may be prepared following the teaching of this invention.

In the selected species used herein for purposes of illustration of the inventive concept, the canine species, a vaccine which stimulates the production of antibodies to the estrogen, estradiol-17 beta, was prepared. The estrogen was reacted with succinic anhydride to form the hemisuccinate and this derivative was coupled to Bovine Serum Albumin (BSA) to form a steriod-protein conjugate against which the immunological system produces antibodies to $E_2$.

It was found that best results could be obtained if from 15 to 25 molecules of the $E_2$ were coupled to each molecule of BSA. It is to be recognized, of course, that a much wider range than this is operable and it is contemplated that a carrier containing attached thereto from about 5 to about 40 molecules of $E_2$ would cause the formation of a sufficient level of antibodies (titer) in the animal to be operable.

One important factor in obtaining satisfactory results with the vaccine of this invention was found to be the antibody level which was produced in the female. A contraceptive effect in female dogs utilizing the claimed vaccine ($E_2$-BSA) can be present if produced anti-$E_2$ titers are maintained at approximately 70 PEA units or above to neutralize endogenously produced $E_2$. It is to be understood, of course, that for different species, different levels of estrogen antibodies may be required. Functionally speaking, sufficient antibodies to effectively neutralize the estrogen levels required for a normal reproductive cycle must be produced.

What is claimed is:

1. A method of inducing a contraceptive effect in a female canine having had at least one previous estrous cycle, which method comprises parenterally administering to said female canine during the period subsequent to estrous, in an amount sufficient to bind at least 70 pg of estradiol-17 beta per ml of serum, an injectable composition capable of preventing conception in a female canine, said injectable composition being produced by a process which comprises the steps of: esterifying the hydroxyl groups of estradiol-17 beta with succinic anhydride to form the estradiol-17 beta hemisuccinate and coupling said hemisuccinate to the amino group of a protein selected from the group consisting of keyhole limpet hemocyanin, bovine serum albumin and human serum albumin, about 5 to about 40 molecules of estradiol-17 beta being bound to each molecule of the protein, to obtain an antigen and emulsifying said antigen in an adjuvant in the order of 1 mg of antigen per 2 mls of adjuvant therefor.

2. The method of claim 1 wherein the protein is bovine serum albumin.

3. The method of claim 2 wherein 15–25 molecules of the estradiol-17 beta hemisuccinate are coupled to each molecule of the bovine serum albumin.

4. The method of claim 1 wherein the estradiol-17-beta succinate is coupled to the protein via the carbodiimide condensation.

* * * * *